Figure 1:
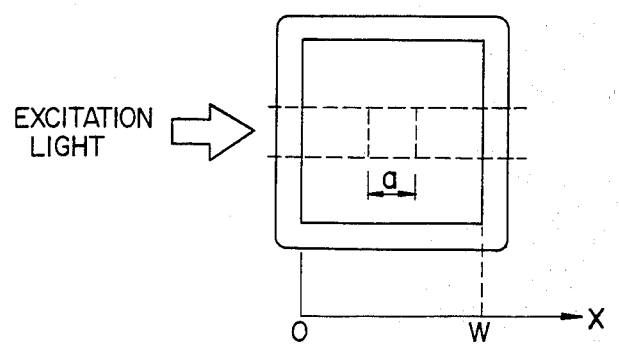

United States Patent [19]

Nogami

[11] Patent Number: 4,531,834
[45] Date of Patent: Jul. 30, 1985

[54] FLUORIMETER

[75] Inventor: Taro Nogami, Katsuta, Japan

[73] Assignee: Hitachi, Ltd., Tokyo, Japan

[21] Appl. No.: 482,248

[22] Filed: Apr. 5, 1983

[30] Foreign Application Priority Data

Apr. 7, 1982 [JP] Japan .................................. 57-56550

[51] Int. Cl.³ .......................................... G01N 21/64
[52] U.S. Cl. ..................................... 356/73; 356/318; 250/458.1
[58] Field of Search ............... 250/458.1, 459.1, 461.1, 250/461.2; 356/73, 317, 318, 417

[56] References Cited

U.S. PATENT DOCUMENTS

| | | | |
|---|---|---|---|
| 3,506,358 | 4/1970 | Baba et al. | 356/319 |
| 3,832,555 | 8/1974 | Ohnishi | 250/458.1 |
| 3,920,334 | 11/1975 | Steichen et al. | 356/73 |
| 4,469,946 | 9/1984 | Tanaka et al. | 250/373 |

FOREIGN PATENT DOCUMENTS

| | | | |
|---|---|---|---|
| 1370300 | 10/1974 | United Kingdom | 250/461.1 |
| 2096352 | 10/1982 | United Kingdom | 356/417 |

OTHER PUBLICATIONS

"Luminescence Spectroscopy-A Versatile Analytical Tool," Harold F. Smith, Research Development, Jul. 1982, p. 20.
Farrand Spectrofluorometer MK-1 Manual Oct. 31, 1968.

*Primary Examiner*—F. L. Evans
*Assistant Examiner*—Joel L. Harringa
*Attorney, Agent, or Firm*—Antonelli, Terry & Wands

[57] ABSTRACT

A fluorimeter comprises an excitation optical system projecting the excitation light having a selected wavelength for a sample to said sample, a sample cell for accommodating the sample; fluorescent light sensors for sensing the fluorescent light emitted from the sample; a transmission light sensor for sensing the light transmitted through the sample; and an arithmetic divider which divides the output of the fluorescent light sensor by the output of the transmission light sensor, and provides a signal representing the intensity of the fluorescent light which is corrected against the variation of the excitation light intensity.

3 Claims, 6 Drawing Figures

FLUORIMETER

The present invention relates to a fluorimeter and, more particularly, to a fluorimeter which accurately compensates the variation of the sensitivity to the fluorescent light caused by the variation of the light source.

Xenon lamps are widely used as a light source of fluorimeters, and such fluorimeters need the compensation for the variation of the light source caused by the deviation of the arc position of the xenon lamp. In addition, in measuring a high concentration sample, in particular, the deterioration of the working characteristics due to the light absorption in the sample must be prevented.

On this account, the conventional fluorimeter employs a beam splitter to divide the light beam from the light source into two before the sample, one being used for exciting the sample, the other as a monitor signal, so that the fluorescence signal from the sample is arithmetically divided by the monitor signal.

U.S. Pat. No. 3,920,334 discloses a "dual purpose detector for a liquid chromatograph" which measures the fluorescent light while monitoring the light transmitted by the sample.

This prior art system, however, does not provide a satisfactory compensation by the following two reasons, and it has a compensation accuracy of around ½.

Figure 2:
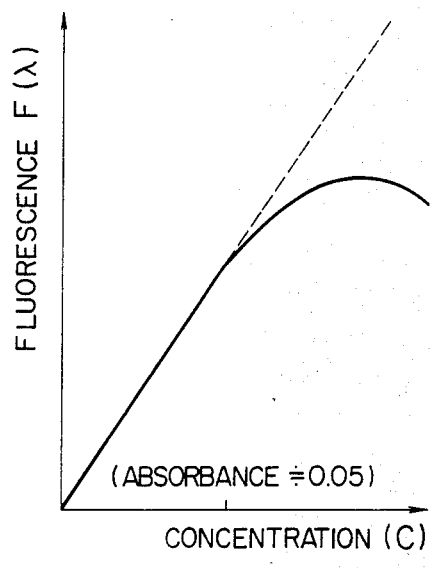

First, displacement of the arc position of the xenon lamp often raises a problem. Displacement of the arc position results in the deviation of the incident beam axis to the fluorimeter, and eventually in a variation of the signal level. In the case of splitting the excitation light beam as employed in the above-mentioned prior art system, the light path for the sample and the monitor light path produce different deviations of light path caused by the variation of the light source, and therefore, the variation of the output cannot be compensated completely by the arithmetic division for the two signals. Second, in measuring a high concentration sample, besides the quenching of light caused by the mutual action among molecules in the sample, the excitation light could be absorbed to an extent beyond a negligible order before it reaches the center of the sample cell. Therefore, the linearity of the working curve is spoiled in the high concentration region, and the above-mentioned prior art split light path system cannot completely recover the linearity. FIGS. 1 and 2 are diagrams explaining the working characteristics. For example, assuming the width between the inner walls of a cell to be w, the width of the image at the position of the sample be a, and setting the x axis in the direction of the beam axis of the excitation light, the intensity of excitation light at a position of x, $I(\lambda,x)$, is given by the following equation.

$$I(\lambda,x) = I(\lambda,O) \exp[-\epsilon(\lambda)c.x] \qquad (1)$$

where $I(\lambda,O)$ is the intensity of the excitation light immediately before entering to the sample, $\epsilon(\lambda)$ is the molar absorptivity, and c is the concentration of the sample.

A small amount of light absorbed in a small width dx in the x direction is given as:

$$dI(\lambda,x) = I(\lambda,x)\epsilon(\lambda)cdx \qquad (2)$$

A small fluorescent light intensity out of the fluorescent light emitted from the small portion dx and received by the fluorescent spectrometer is given as:

$$dF(\lambda,x) = (g/n^2)QI(\lambda,x)\epsilon(\lambda)cdx \qquad (3)$$

where g is the geometric constant, n is the refractive index of the solution, and Q is the quantum efficiency of the sample.

In practice, the fluorescent light emitted from a section a in FIG. 1 is received by the fluorescent spectrometer, and the fluorescent light intensity observed is given as follows.

$$F(\lambda) \int_{\frac{w}{2}-\frac{a}{2}}^{\frac{w}{2}+\frac{a}{2}} dF = (g/n^2)QI(\lambda,0)\epsilon(\lambda)c \times \int_{\frac{w}{2}+\frac{a}{2}}^{\frac{w}{2}+\frac{a}{2}} \exp[-\epsilon(\lambda)cx]dx \qquad (4)$$

FIG. 2 shows by the solid line the relationship between the concentration c and the fluorescent light intensity $F(\lambda)$ based on Equation (4), indicating that the linearity of the working curve is spoiled significantly in the high concentration region.

It is an object of the present invention to provide an apparatus for compensating the detection output signal level affected by the variation of the light source that cannot be achieved completely by the foregoing prior art split light path system.

In order to achieve the above-mentioned object, one feature of the present invention is to detect the sample transmission light by means of a transmission light sensor provided at the rear of the sample cell, instead of splitting the excitation light before the sample, and using the sensor output as a correction signal. For many low concentration samples, the arrangement is made such that the fluorescent light intensity is arithmetically corrected by the transmission light intensity.

In measuring a high concentration sample, if the working curve deviates in excess of the variation of the detection output signal caused by the variation of the light source, the square root of the transmission light intensity is preferably used for the divisor of the calculation. The significance of using the square root of the transmission light intensity in division for making correction of a high concentration sample is substantially identical, as will be described later, to the significance of using the transmission light intensity in division for a low concentration sample as mentioned previously.

Figure 3:
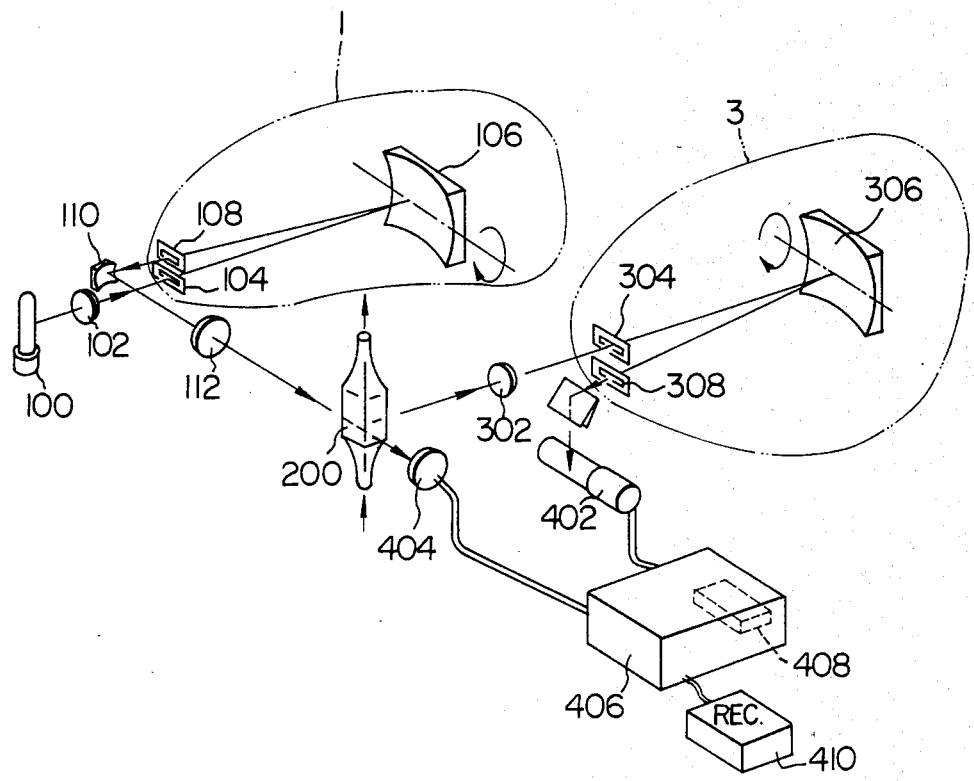
Figure 4:
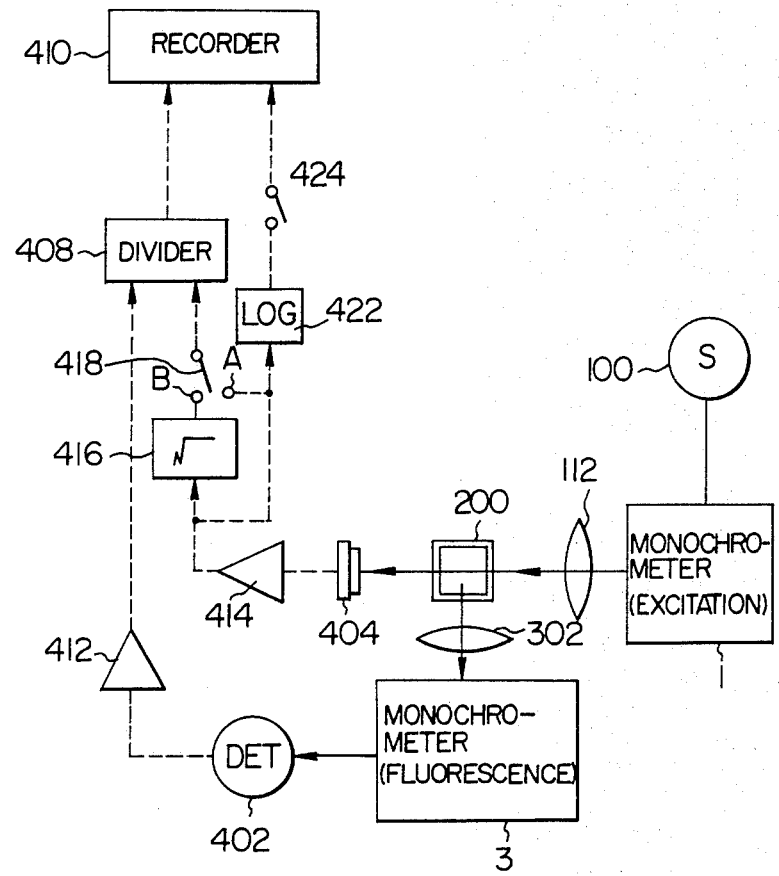
Figure 5:
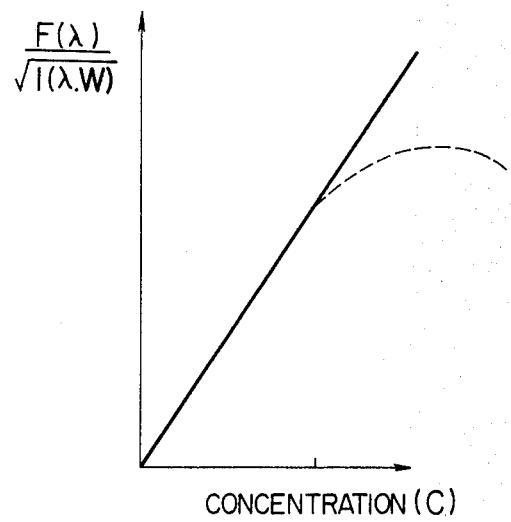
Figure 6:
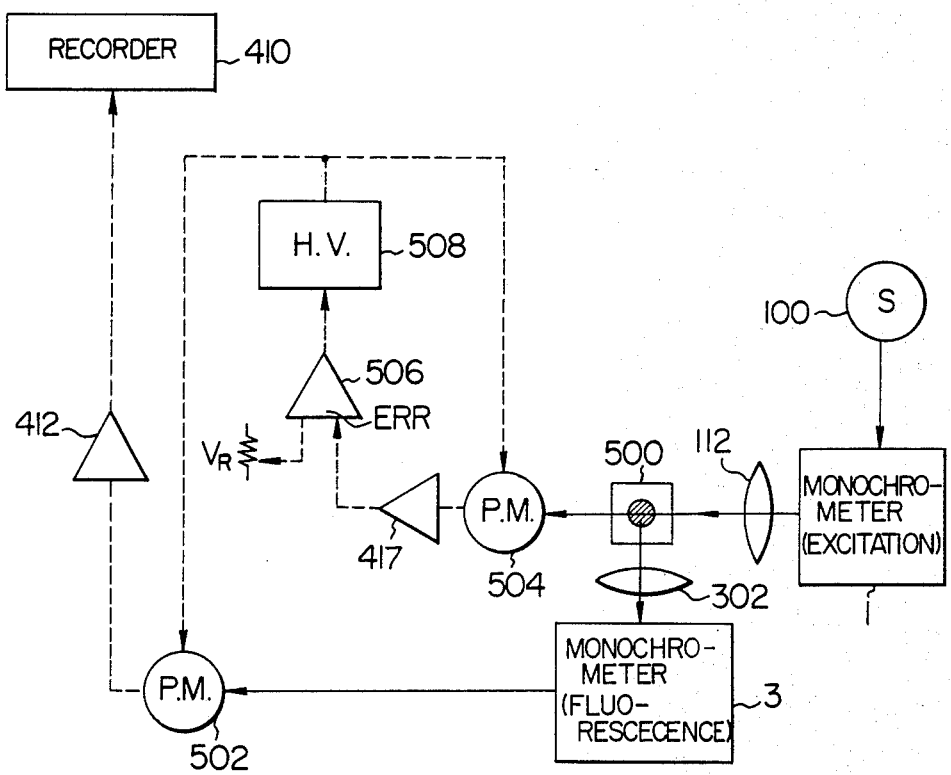

The present invention will be apparent from the following detailed description taken in conjunction with the accompanying drawings, in which: FIG. 1 is an illustration showing the measurement for a sample cell; FIG. 2 is a graph showing the working characteristics of the conventional fluorimeter plotted against the concentration of the sample on the logarithmic scale; FIG. 3 is an illustration showing the basic principle of the fluorimeter embodying the present invention; FIG. 4 is a systematic diagram showing another embodiment of the present invention, which allows the measurement of a high concentration sample; FIG. 5 is a graph showing the working characteristics of the embodiment shown in FIG. 4 plotted against the concentration of the sample; and FIG. 6 is a systematic diagram showing still another embodiment of the present invention.

The present invention will now be described by way of an embodiment with reference to the drawings.

In FIG. 3 showing the principle of an embodiment of the present invention, the light emitted from a light source 100 is converged by a lens 102, passed for dispersion through an exciter's monochromater made up of an input slit 104, a concave diffraction grating 106 and an output slit 108, converged by a toroidal mirror 110 having different curvatures in the lateral and longitudinal directions and a lens 112, then conducted into a flow cell 200. The fluorescent light emitted by a sample in the flow cell is converged by a lens 302, passed through a fluorescent monochromater made up of an input slit 304, a concave diffraction grating 306 and an output slit 308, conducted into a fluorescent measurement sensor 402, then converted into a signal representing the intensity of the fluorescent light. On the other hand, the excitation light transmitted through the flow cell 200 is received by a photo-cell 404, so that it is converted into a signal representing the intensity of the transmission light. These signals representing the intensity of the fluorescent light and transmission light are processed by a processor 406. The processor 406 incorporates an arithmetic divider 408, by which the signal representing the intensity of the fluorescent light is divided by the signal representing the transmission light. The output of the processor 406 is visualized by an output unit 410 such as a recorder. Whereas the fluorimeter for liquid chromatography is entirely used for samples of low concentration, the arrangement of FIG. 3 having a very short light path for the excitation light transmitting through the sample enables the light absorption factor of the excitation light to be as small as 0.01 to 0.001. Accordingly, even if the division operation for the correction of variation of the light source is carried out using the transmission light instead of the excitation light at the center of the sample, the influence of light absorption by the sample can be neglected. Use of the sample transmission light as the correction signal overcomes the incomplete correction caused by the inconsistent effects of light source variation as seen in the conventional split light path system, and the influence of the light source variation can be corrected accurately. Although this embodiment is a fluorimeter for liquid chromatography, the invention is applicable to many other fluorimeters using normal sample cells other than flow cells.

FIG. 4 shows another embodiment of the present invention, which allows the measurement of high concentration samples as well as low concentration samples.

The light emitted from a light source 100 is passed through a exciter's monochromater 1, for dispersion, converged by a convergence mirror 112, then conducted to a sample cell 200. The fluorescent light emitted by the sample within the sample cell is converged by a convergence mirror 302, passed through a fluorescent monochromater 3, then converted into a signal representing the intensity of the fluorescent light by a fluorescence measurement sensor 402. On the other hand, the light transmitted through the sample cell 200 is received by a photo-cell 404 so that it is converted into a signal representing the intensity of the transmission light. The fluorescence signal is amplified by an amplifier 412, and then received by one input of a divider 408. Switch 418 is set to the side of contact B for the measurement of a high concentration sample. The transmission light signal is amplified by an amplifier 414, converted into the value of square root by a square root calculator 416, then conducted through the contact B of the switch 418 to another input of the divider 408. The divider 408 divides the fluorescent light output by the square root of the transmission light output, and the result of division is sent out to a recorder 410. As shown in FIG. 1, when the sample cell has an inner wall space of w, the fluorescent light is received by the fluorescent spectro-photometer at a point when the light goes in the sample by a distance of w/2, since the axis of the fluorescent optical system passes the center of the cell. On the other hand, the photo-cell 404 for the transmission light receives the light which goes in the sample by a distance of w.

Placing the intensity of light exciting the sample at the center of the cell to be $I(\lambda, w/2)$ and the intensity of light received by the photo-cell be $I(\lambda,w)$, the following equations are formed.

$$I(\lambda, w/2) = I(\lambda, O)\exp[-\epsilon(\lambda)cw/2] \quad (5)$$

$$I(\lambda, w) = I(\lambda, O)\exp[-\epsilon(\lambda)cw] \quad (6)$$

Taking a square root of Equation (6) and interchanging the right and left terms gives:

$$\sqrt{I(\lambda,0)} \ \exp[-\epsilon(\lambda)cw/2] = \sqrt{I(\lambda,w)} \quad (7)$$

Substitution of Equation (7) into the right term of Equation (5) gives:

$$I(\lambda, w/2) = \sqrt{I(\lambda,0)} \times \sqrt{I(\lambda,w)} \quad (8)$$
$$= \text{Const.} \times \sqrt{I(\lambda,w)}$$

Accordingly, it is understood that the square root of the transmission light intensity is in proportion to the excitation light intensity at the center of the sample. That is, division of the signal representing the fluorescent light intensity by the signal of the transmission light which is converted into the square root value by the square root calculator 416 signifies the division by the value proportional to the excitation light intensity $I(\lambda, w/2)$ at the center of the sample. Both of the use of the square root of the transmission light intensity in the division operation in correcting the measurement for a high concentration sample and the use of the transmission light intensity for the division operation in correcting the measurement for a low concentration sample substantially signify the proper correction for the excitation light intensity at the center of the sample. Accordingly, the fluorescent light intensity irrespective of the quenching or absorption of the excitation light by the sample can be obtained. This value is in proportion to the concentration of the sample, and it means the extension of linearity of the working curve to the high concentration region. FIG. 5 shows the improvement of the linearity. It is understood from the figure that the output value shown by the solid line which is calculated by dividing the fluorescent light intensity $F(\lambda)$ by the square root of the transmission light intensity, $\sqrt{I(\lambda,w)}$ maintains the linearity in the high concentration region.

Accordingly, the embodiment shown in FIG. 4 is capable of correcting the signal level without spoiling the linearity of working characteristics up to the high concentration region of samples. In addition, the arrangement is made so that the transmission light intensity is supplied directly to the divider 408 without being converted into the square root value by turning over the switch 418 for the measurement of low concentration samples.

Subsequently, the output of the photo-cell 404 for the transmission light is amplified by the amplifier 414, converted into a logarithmic value by a logarithmic converter 422, and sent through a switch 424 to the recorder 410 so that it is displayed together with the result of fluorescence measurement. This makes it possible to effect the concurrent measurement for the degree of light absorption and the fluorescent light intensity. In the prior art system, it is not possible to measure the fluorescence in a low concentration region where the light absorption is measured, due to the curving of the working curve for the fluorescence measurement. However, according to the present invention, as described above, the concurrent measurement is made possible. This allows the comparison between the degree of light absorption and the degree of fluorescence at the same concentration of the sample, and much information for the qualitative analysis can be obtained.

By addition of a means for calculating the ratio of the degree of fluorescence to the degree of light absorption, the calculation for the quantum absorption rate is also made possible.

FIG. 6 shows still another embodiment of the present invention, where the identical functional components to those of FIG. 4 are referred to by the common reference numbers. The light from an arc light source such as a xenon lamp or from a light source 100 of producing a ultraviolet continuous spectrum such as a metallic halide lamp is dispersed by an exciter's monochromater 1 and conducted through a lens 112 to a flow cell 500. The light transmitted through the sample in the flow cell 500 is received by a photo-multiplier 504 so that it is converted into a signal representing the intensity of the transmission light. This signal is conducted through an amplifier 417 to one terminal of an error signal amplifier 506 which has two inputs. The amplifier 417 includes a square root calculator so as to provide a signal proportional to the square root of the signal from the photomultiplier 504 to the error signal amplifier 506. Another terminal of the amplifier 506 is connected to a reference voltage source $V_R$, and the amplifier provides a voltage corresponding to the difference of the voltages at the two input terminals to a high voltage circuit 508. The fluorescent light emitted by the sample in the flow cell 500 is converged by a lens 302, passed through a fluorescence spectrometer 3, and conducted to a photo-multiplier 502.

The output of the high voltage generator 508 is conducted to the gain control terminals of the two photo-multipliers 502 and 504 so as to control the ratio of the output signal level to the input light for each of the photo-multipliers. The photo-multiplier 504, amplifier 414, error signal amplifier 506, and high voltage circuit 508 constitute a closed loop circuit. This circuit arrangement provides a negative feedback for the photo-multiplier 504, and at the same time the same gain control acts on the photo-multiplier 502. This feedback is based on the diode effect of the photo-multiplier, and is generally called "analog photo-multiplier diode feedback". The photo-multiplier 502 provides at its output the fluorescence intensity signal under the condition of providing an ever-constant transmission light intensity. This signal may be assumed to have been corrected for the light source variation as in the case of the embodiment shown in FIG. 4 with the switch 418 being set to contact A, and is sent through an amplifier 412 to the recorder 410.

According to the present invention, as described above, the effect of the light source variation is improved significantly for usual samples. Particularly, in cases where the shift of the light emitting point in the light source is in question, the accuracy of correction can be improved by ⅓ to ¼ as compared with the accuracy of correction by the prior art colorimetry.

For high concentration samples, the nonlinearity of the working curve can be corrected effectively. This allows not only the extension of the high concentration region for the qualitative analysis, but the concurrent measurement of the degree of light absorption and the intensity of fluorescent light. Consequently, the qualitative analysis can be made more accurate, and the calculation for the quantum efficiency rate can be made easier.

What is claimed is:

1. A fluorimeter comprising:
   an excitation optical system projecting excitation light with a wavelength selected for a sample into said sample;
   a sample cell accommodating said sample;
   fluorescence sensing means sensing the fluorescent light emitted by said sample;
   transmission light sensing means sensing the light transmitted through said sample;
   arithmetic division means dividing the output of said fluorescence sensing means by the output of said transmission light sensing means and providing a signal representing the intensity of the fluorescent light so that the variation of the intensity of said excitation light is corrected; and
   a square root calculator provided between said transmission light sensing means and said division means, and adapted to calculate the square root of the output signal from said transmission light sensing means, said division means dividing arithmetically the output of said fluorescence sensing means by the output of said square root calculating means.

2. A fluorimeter according to claim 2, further comprising a logarithmic converter connected to said transmission light sensing means which performs longarithmic calculation for the output of said transmission light sensing means and which provides an output signal indicative thereof.

3. A fluorimeter comprising:
   a light source;
   a first monochromater on the side of excitation passing the light emitted by said light source so as to provide the excitation light having a wavelength suitable for a sample;
   a sample cell having three transparent windows for introducing said excitation light to a sample accommodated in said sample cell, outputting the fluorescent light excited by said excitation light, and outputting the light transmitted through said sample, respectively;
   a second monochromater on the side of the fluorescence receiving and dispersing said excited fluorescent light;
   a transmission light photo-multiplier with control input terminal which receives said transmission light and provides an electrical signal representing the intensity of said transmission light;

a fluorescence photo-multiplier with control input terminal which receives the fluorescent light provided by said second monochromater and provides an electric signal representing the intensity of said fluorescent light;

an error signal aplifier which receives said electrical signal representing the intensity of said transmission light and a reference signal, and provides a differential voltage corresponding to the difference of the voltage of the received signals;

a high voltage generator which receives said differential voltage and provides a high voltage corresponding to said differential voltage to said transmission light photo-multiplier and said fluorescence photo-multiplier in order to control the converting amplification factor of the input light vs. electrical output signal relationship for said transmission light photo-multiplier and said fluorescence photo-multiplier concurrently;

an amplifier which amplifies sid fluorescence electrical signal and provides an fluorescence intensity signal which is corrected against the variation of excitation light intensity caused by the variation of said light source; and an amplifier which receives said transmission light electrical signal and provides a signal proportional to the square root of said transmission signal to said error amplifier as the electrical signal representing the intensity of said transmission light, so that light absorption in measuring a high concentration sample is corrected.

* * * * *